United States Patent [19]

Weismann et al.

[11] Patent Number: 5,303,700
[45] Date of Patent: Apr. 19, 1994

[54] METHOD FOR DETECTING THE RESPIRATORY PHASES OF A PATIENT DURING AN ASSISTED VENTILATING PROCESS

[75] Inventors: Dieter Weismann, Grönau; Marcel Baum, Oberhofen-Telfs, both of Fed. Rep. of Germany

[73] Assignee: Drägerwerk Aktiengesellschaft, Lübeck, Fed. Rep. of Germany

[21] Appl. No.: 908,972

[22] Filed: Jul. 6, 1992

[30] Foreign Application Priority Data

Jul. 4, 1991 [DE] Fed. Rep. of Germany ........ 4122069

[51] Int. Cl.$^5$ ............................................ A61M 16/00
[52] U.S. Cl. .......................... 128/204.23; 128/204.18; 128/204.21; 128/204.26
[58] Field of Search ...................... 128/204.18, 204.21, 128/204.23, 204.26

[56] References Cited

U.S. PATENT DOCUMENTS 3,834,382  9/1974  Lederman et al. ............. 128/204.24
4,050,458  9/1977  Friend ........................... 128/204.23

Primary Examiner—Edgar S. Burr
Assistant Examiner—Aaron J. Lewis
Attorney, Agent, or Firm—Walter Ottesen

[57] ABSTRACT

The invention relates to a method for recognizing the respiratory phases of a patient for controlling a ventilating apparatus. The time-dependent trace of a signal, which represents the respiratory flow curve and is emitted by a signal device, is determined and from this trace, a trigger criterium is obtained for the switchover of the ventilating apparatus from the expiration phase into the inspiration phase and/or from the inspiration phase into the expiration phase. The method is improved in that even for chronically obstructive patients, a reliable and early recognition of the inspiration and expiration attempts is possible. A significant increase of the slope of the respiratory flow curve between each two zero crossovers of this curve is used as a trigger criterium.

9 Claims, 1 Drawing Sheet

METHOD FOR DETECTING THE RESPIRATORY PHASES OF A PATIENT DURING AN ASSISTED VENTILATING PROCESS

FIELD OF THE INVENTION

The invention relates to a method for detecting the respiratory phases of a patient for controlling a ventilating apparatus. The time-dependent trace of a signal, which represents the respiratory flow curve and is emitted by a signal device, is determined and a trigger criterium for the reversal of the ventilating apparatus is obtained from this trace. This reversal of the ventilating apparatus is from the expiration phase into the inspiration phase and/or from the inspiration phase into the expiration phase.

BACKGROUND OF THE INVENTION

For patients with healthy lungs, no significant phase shift exists between the force response of the respiratory muscles and the resulting respiratory flow. For this reason, a good respiratory phase identification can be derived from the zero crossovers of the mouth pressure or respiratory flow as they are required as a trigger criterium for the phase reversal during assisted ventilating forms.

U.S. Pat. No. 3,834,382 discloses a ventilating apparatus wherein the zero crossover of the respiratory flow curve is used as a trigger criterium. This method however is deficient when the time constant of the lung with reference to the duration of the respiratory phases increases as is the case for chronically obstructive patients (COPD) at increased breathing frequency. A phase shift occurs between the force response of the respiratory muscles and the resulting respiratory flow. A discoordination between the activity of the respiratory muscles and the flow direction in the respiratory tract is observed and thereby the externally recognizable respiratory phases.

An assisted ventilating method which undertakes the reversal of inspiration to expiration or from expiration to inspiration pursuant to methods of respiratory phase identification used today can, in such patients, contribute to an unwanted increase of the isometric respiratory work. The patient senses the initiation of the inspiration assistance as being too late; on the other hand, the patient already initiates an expiration even though the ventilating apparatus still continues to supply volume to the lung.

U.S. Pat. No. 4,050,458 discloses a ventilating apparatus wherein the time trace of the mouth pressure of the patient is measured and, by forming the second time differential, a kink point in the end phase of the expiratory pressure trace is determined. This kink point acts as a trigger criterium for the inspiration phase which follows. It is a disadvantage of this apparatus that a reliably evaluatable pressure signal is only obtained when the ventilating apparatus has an unwanted high flow resistance. For conventional flow resistances, the pressure signal is so small that it merges with noise. Furthermore, it is a disadvantage that no trigger criterium can be obtained for the reversal from inspiration to expiration.

SUMMARY OF THE INVENTION

In view of the foregoing, it is an object of the invention to provide a method for identifying the respiratory phases of a patient for controlling a ventilating apparatus. The time trace of a signal, which represents the respiratory flow curve and is emitted by a signal device, is determined and, from this trace, a trigger criterium is obtained for the reversal of the ventilating apparatus from the expiration phase to the inspiration phase and/or from the inspiration phase to the expiration phase. The method of the invention makes possible a reliable and early identification of the inhaling and exhaling attempts even for chronically obstructive patients.

According to a feature of the invention, a significant increase of the slope of the respiratory flow curve is used as a trigger criterium between each of the zero crossovers of this curve.

The advantage of the invention is that with the method, every attempt by the patient to inhale or exhale is identified even when a phase shift is present between the force response of the respiratory muscles and the resulting respiratory flow. A reliable evaluation of the measured values is possible by the use of a signal representing the respiratory flow.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
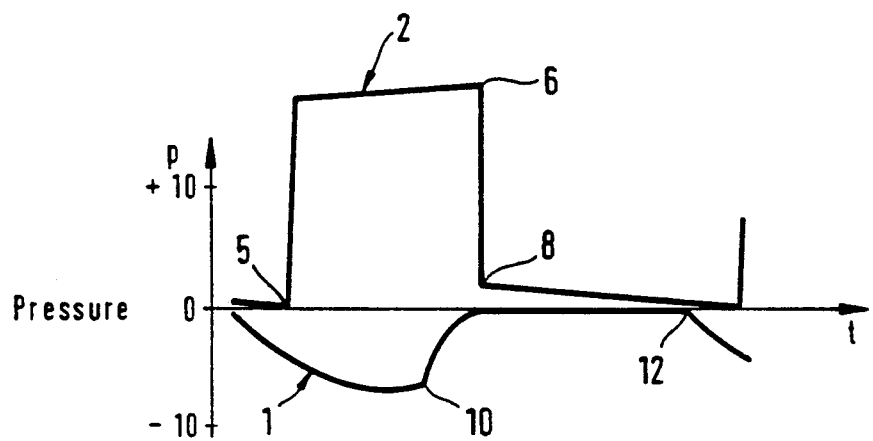
FIG. 1 is a graph with arbitrary units of measured values of pressure and flow as a function of time as they result for a ventilation of a chronically obstructive patient pursuant to known methods; and, FIG. 2 shows, as a comparison, the corresponding curves which result with the method according to the invention.

The upper curve of FIG. 1 shows the pleural pressure 1 and the respiratory tract pressure 2. The pleural pressure is the pressure between the lung and the thorax cage of the patient and defines a measure for the activity of the respiratory muscles. The respiratory tract pressure is the pressure of the respiratory gas at the mouth of the patient.

The respiratory flow 3 is shown in the lower portion of FIG. 1.

The curves start with the end phase of an expiration. The zero crossover 4 of the respiratory flow 3 serves the ventilating apparatus operating pursuant to the known method as a trigger criterium for the switchover to inspiration. At the instant 5, the respiratory tract pressure 2 generated by the ventilating apparatus increases and, as a consequence, the respiratory flow 3 also suddenly increases. The respiratory tract pressure 2 increases slightly up to the end 6 of the inspiration phase; whereas, the respiratory tract flow 3 drops continuously. At the instant 6, the respiratory flow has dropped to 25% of its maximum value 7. This instant 6 serves the ventilating apparatus operating pursuant to the known method as a trigger criterium for the switchover to expiration.

The respiratory tract pressure 2 then drops suddenly to a very low value 8 which results from the respiratory flow and the flow resistance of the ventilating apparatus and the respiratory flow 3 becomes negative. The respiratory tract pressure 2 and the absolute amount of the respiratory flow 3 then drop continuously until, at a new zero crossover 9 of the respiratory flow, a new inspiration phase is initiated by the ventilating apparatus.

If the pleural pressure 1 is now considered, then it is seen that, in the first part of the inspiration phase, the pleural pressure becomes continuously more negative. This means that the patient has tensioned the respiratory muscles in order to inhale.

At a point 10, the curve suddenly breaks and the pleural pressure slowly drops toward zero. The kink point 10 shows that the patient has relaxed the respiratory muscles and wants to exhale. Because of the narrowing of the respiratory tract, the respiratory flow 3 does not drop sharply. At the time point 10, only a change of the slope 11 of the respiratory flow 3 occurs and, at the time point 10, the pleural pressure curve 1 breaks downwardly. However, the ventilating apparatus only reacts when the respiratory flow has dropped to 25% of the maximum value as shown at point 6; that is, the ventilating apparatus switches over much later to expiration than the patient would want. In FIG. 1, the time from the attempt of the patient to exhale up to the switchover of the ventilating apparatus is represented by $t_{del}$.

The drop 12 of the pleural pressure curve 1 shows the attempt by the patient to inhale. A change of the slope 13 is shown again in the respiratory flow curve 3. The ventilating apparatus however only responds much later, namely, when the respiratory flow passes through zero as indicated at reference numeral 9.

For an attempt by the patient to inhale, the slope of the respiratory flow curve 3 changes essentially in that the curve runs at a greater slope than previously toward the zero line (points 11 and 13 in curve 3), that is, the slope of the respiratory flow curve increases.

Figure 2:
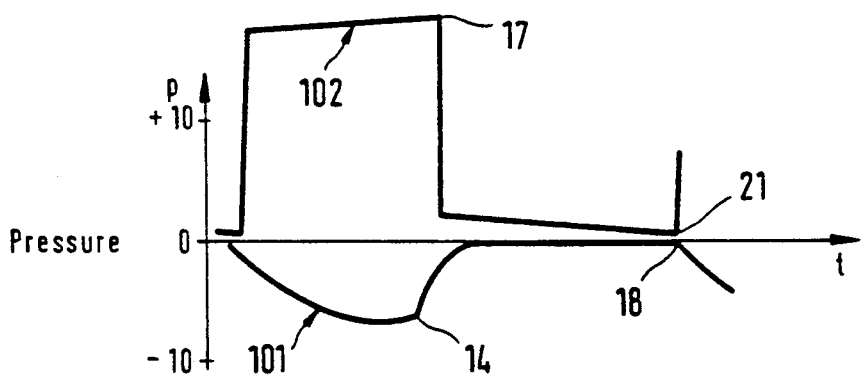

In FIG. 2, the corresponding curves are shown of the pleural pressure 101, the respiratory tract pressure 102 and the respiratory flow 103 which result with a ventilating apparatus operating pursuant to the method of the invention.

The kink 14 in the curve of the pleural pressure 101 characterizes the instant at which the patient desires to exhale. At this instant, the slope of the respiratory flow curve 103 changes (point 15). The ventilating apparatus already recognizes this change of slope a very short time later and initiates the expiration phase (point 16). The respiratory tract pressure 102 drops (point 17) and the respiratory flow 103 becomes negative.

The falling pleural pressure (point 18) shows that the patient desires to inhale. At the same instant (point 19), the slope of the respiratory flow curve 103 changes and the ventilating apparatus switches over to inspiration a short time later (point 20). The respiratory tract pressure 102 increases (point 21) and the respiratory flow 103 becomes positive.

The time which lies between the attempt by the patient to inhale (exhale) and the response of the ventilating apparatus is, with the method of the invention ($t_{del}$ in FIG. 2) considerably less than for the known method ($t_{del}$ in FIG. 1). In this way, the patient is ventilated in a considerably more gentle manner.

The respiratory flow curves (3, 103) to be evaluated can be obtained in various ways. For example, a flow sensor which is known in various configurations can be built into the respiratory gas line of the ventilating apparatus and the electrical output signal of this flow sensor then represents the respiratory flow curve. A flow sensor can be omitted in ventilating apparatus wherein a flow control valve is, for example, so driven that the respiratory tract pressure (curves 2 or 102) is always held to a desired curve. The control signal of the flow control valve then represents the respiratory flow curve.

According to the invention, an increase of the slope of the respiratory flow curve acts as a trigger criterium for the switchover of the ventilating apparatus. The instant of switchover at which the respiratory flow curve passes through zero defines the greatest occurring increase of the slope; however, this increase should not act as a trigger criterium since, otherwise, the ventilating apparatus would switch over the respiratory phases continuously at high frequency. The time point for identifying a trigger criterium must therefore be limited to a time interval between each of the zero crossovers of the respiratory flow curve.

Furthermore, during a short time span after a switchover of the respiratory phase, transient operation of the ventilating apparatus causes fluctuations in the respiratory flow curve which could be identified as a trigger criterium in an unwanted manner. The switchover into the other respiratory phase is generally only then purposeful after a time has elapsed since the last switchover which results from the reciprocal value of twice the maximum permissible respirating frequency.

For the above reasons, it is purposeful to provide an ancillary critèrium for the validity of the trigger criterium and in this way preclude unwanted premature triggering. This can take place in that only a significant increase of the slope of the respiratory flow curve is used as a trigger criterium. This significant increase occurs after the particular extreme value of the respiratory flow curve is exceeded.

A still greater reliability against unwanted triggering is obtained if only a significant increase of the slope of the respiratory flow curve is used as a trigger criterium. The increase occurs after a delay time has passed starting with each zero crossover of the respiratory flow curve.

The delay time must be at least so long that the above-mentioned transients have decayed to the extent that they no longer disturb the recognition of the trigger criterium. This time is dependent upon the characteristics of the ventilating apparatus and a value of approximately 50 ms can be assumed as a lower limit. The maximum delay time must be shorter than the time which results from the reversal value of twice minimal permissible respiratory frequency. One second results with a respiratory frequency of 30 per minute. As an upper limit for the delay time, a value of 800 ms can be set under these conditions. The described coupling of the trigger criterium to an ancillary criterium (exceeding the extreme value or delay time) can be carried out with known means such as logic electronic circuits or in a computer by means of suitable program commands.

An increase of the slope of the respiratory flow curve can then be seen as significant for the recognition of the trigger criterium when this increase takes place within a specific time interval (between the zero crossovers or after exceeding the extreme value of the respiratory flow curve or after a delay time has run) and when this increase of slope exceeds an amount which can be fixed. This measure is fixed so that a triggering is not initiated in an unwanted manner because of signal fluctuations (noise) or a nonlinear trace of the respiratory flow curve. The respiratory flow curve becomes very nonlinear when, for example, the ventilating apparatus supplies a variable respiratory tract pressure during the inspiration phase. With appropriate electronic means, it is possible to determine the change of the slope of the respiratory flow curve which is caused by variable respiratory tract pressure and to subtract from the measured change of the slope of the respiratory flow curve. The difference then defines primarily the significant change of the slope of the respiratory flow curve with this change being caused by an effort by the patient to inhale or exhale.

The increase of the slope of the respiratory flow curve which serves as a trigger criterium for the switchover of the respiratory phases can be detected in various ways.

One possibility is that the signal, which represents the respiratory flow curve (3, 103) is first made smooth by a low pass in order to reduce signal noise. Then, the second time differential is formed. The signal obtained in this manner is a measure for the curvature of the respiratory flow curve. In the embodiment of FIG. 1, this signal is slightly positive from point 7 to point 11 and becomes clearly negative at point 11. This significant change of the signal can be distinguished from small signal fluctuations occurring because of residual noise and nonlinearity of the respiratory flow curve by means of a threshold value circuit. The signal occurring rearward of the threshold value circuit then shows a significant change in the slope of the respiratory flow curve and can be conducted to a trigger circuit of the respiratory apparatus. This trigger circuit then switches the respiratory apparatus from one respiratory phase to the other. At this instant, the slope of the respiratory flow curve changes greatly (points 16 and 20 in curve 103, FIG. 2) which, in turn, leads to a signal at the output of the threshold value circuit. This signal should not however serve as a trigger criterium and can be suppressed by means of a logic circuit.

A further possibility to find the trigger criterium is to adapt a mathematical function to the respiratory flow curve in the time between respective zero crossovers. A polynome of the n-th order or an exponential function can be applied as a mathematical function. The simplest case is the adaptation of a straight line. For this purpose, the trace of a specific time disposed forward of the actual time is extrapolated linearly into the future.

Starting from the kink points (15, 19) of the respiratory flow curve 103, the measured values 103 deviate increasingly from the values computed with the adapted function. In order to distinguish a deviation, which is caused by the respiratory activity of the patient, and is usable as a trigger criterium from a deviation caused, for example, by signal noise, the deviation must exceed a pregiven amount in order that it be seen as significant. If this amount is exceeded (points 16 and 20, FIG. 2), a signal is supplied to the trigger circuit of the ventilating apparatus.

The adaptation of the functions for inspiration and expiration can also be averaged over several inspirations. Averaged parameters for the drop of the absolute amount of the respiratory flow in inspiration and expiration result from the functions. With these parameters and the particular measured extreme values of the respiratory flow curve, the probable trace of the respiratory flow curve can then be precalculated. A significant deviation of the measured trace from the precalculated trace then serves as a trigger criterium.

In a last embodiment of the invention, a mathematical model of the lung of the patient and of the ventilating apparatus are placed into a computer which runs synchronously to the ventilating. The model parameters (for example compliance and resistance of the lung as well as the respiratory tract pressure) are continuously adapted to the measured values of the respiratory flow curve. In this computer model, the increases of the slope of the respiratory flow curve (points 15 and 19, FIG. 2) are recognized by the computer program and serve as trigger criterium for the switchover of the ventilating apparatus. As an alternative hereto, a deviation of the measured from the computed respiratory flow curve serves as a trigger criterium.

The above embodiments of the method of the invention can be realized by means of analog electronics such as an analog computer or can be carried out in a computer after the measured values have been digitalized.

It is understood that the foregoing description is that of the preferred embodiments of the invention and that various changes and modifications may be made thereto without departing from the spirit and scope of the invention as defined in the appended claims.

What is claimed is:

1. A method for detecting the respiratory phases of a patient for controlling a ventilating apparatus, the method comprising the steps of:

determining the time-dependent trace of a signal supplied by a signal device with said signal representing a respiratory flow curve which crosses zero with each change in flow direction so as to provide sequential zero crossovers and which has a changing slope between each two successive ones of the zero crossovers;

determining a trigger criterium from said trace for switching over the ventilating apparatus from the expiration phase to the inspiration phase and/or from the inspiration phase to the expiration phase by examining said trace to locate a significant increase in the slope within each time interval having a start which lies after each one of said zero crossovers and which ends at the next zero crossover; and, utilizing each of said significant increases in said slope as said trigger criterium.

2. The method of claim 1, further comprising:

low-pass filtering said signal and then forming the second derivative as a function of time; and, utilizing a change of the signal obtained in this manner as a trigger criterium with said change representing a significant increase in the slope of said curve.

3. The method of claim 1, comprising the further steps of:

running a computer model of the patient's lung and the ventilating apparatus synchronously to the ventilation of the patient while continuously adapting the model parameters to the measured respiratory flow curve; and, utilizing the increase of the slope of the computed respiratory flow curve occurring in the computer model as said trigger criterium.

4. The method of claim 3, comprising the further step of utilizing a significant deviation of the measured trace of the respiratory flow curve from the trace of the respiratory flow curve precalculated with said computer model as said trigger criterium.

5. The method of claim 1, comprising the further steps of:

examining said trace to locate an extreme value between each two successive ones of said crossovers; and, selecting said extreme values as the start of the corresponding time interval.

6. The method of claim 5, comprising the further steps of:
adapting a mathematical function to said respiratory flow curve;
obtaining parameters between each two successive ones of the zero crossovers of said respiratory flow curve averaged over several breaths for the drop of said curve during inspiration and expiration phases;
calculating in advance the trace of said curve from said parameters and said extreme value; and,
utilizing the occurrence of a significant difference between said trace and said curve as said trigger criterium.

7. The method of claim 1, comprising the further steps of:
selecting a delay time measured from each of the zero crossovers; and,
determining each of the starts as being coincident with the end of the delay time.

8. The method of claim 7, comprising the further step of selecting said delay time to have a value in the range of 50 ms to 800 ms.

9. The method of claim 1, comprising the further steps of:
adapting a mathematical function to said respiratory flow curve between each two successive ones of said zero crossovers; and,
utilizing a significant departure of said respiratory flow from said mathematical function as said trigger criterium.

* * * * *